United States Patent [19]

Vilkomerson

[11] 4,407,294

[45] Oct. 4, 1983

[54] ULTRASOUND TISSUE PROBE LOCALIZATION SYSTEM

[75] Inventor: David H. R. Vilkomerson, Princeton, N.J.

[73] Assignee: Technicare Corporation, Solon, Ohio

[21] Appl. No.: 337,908

[22] Filed: Jan. 7, 1982

[51] Int. Cl.³ .............................................. A61B 10/00
[52] U.S. Cl. .................................................... 128/660
[58] Field of Search ................................ 128/660–663, 128/24 A, 75 A

[56] References Cited

U.S. PATENT DOCUMENTS 3,542,014 11/1970 Peronneau .................... 128/24 A
3,676,584 7/1972 Plakos et al. ................ 128/24 A X
4,273,111 6/1981 Tsukaya ....................... 128/660 X

FOREIGN PATENT DOCUMENTS 2907504 9/1980 Fed. Rep. of Germany ...... 128/660
7513862 6/1976 Netherlands ....................... 128/660

Primary Examiner—Kyle L. Howell
Assistant Examiner—Francis J. Jaworski

[57] ABSTRACT

A novel pulse-echo ultrasound imaging system is disclosed comprising at least three transducers. A first external scanning transducer images a selected scan area of body tissue by pulsing that area with ultrasonic waves. Two additional detector-transducers are disposed at distinct locations on a probe, such as a biopsy needle, which is inserted into the body in the vicinity of the scan area. By determining the sequence of wave front arrivals at the detectors-transducers, the relative location of the probe with respect to the scan area is readily determined and indicated. Either the scanning transducer or the probe may then be maneuvered in response to such indication to ensure that the probe tip is properly positioned relative to the scan area.

10 Claims, 3 Drawing Figures

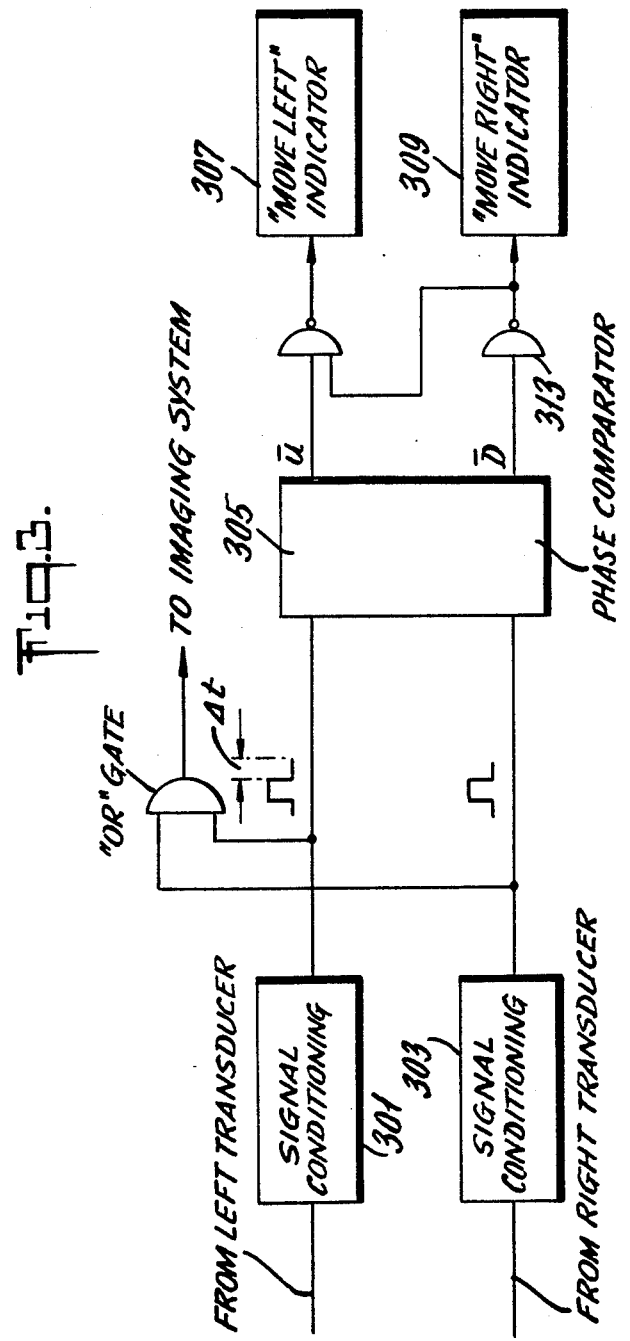

ULTRASOUND TISSUE PROBE LOCALIZATION SYSTEM

CROSS REFERENCE TO RELATED PATENTS

The present application is related to U.S. Pat. No. 4,249,539, dated Feb. 10, 1981, which is assigned to the assignee of the present application, and is hereby incorporated by reference as if fully set forth herein.

BACKGROUND OF THE INVENTION AND PRIOR ART

The present invention relates to the field of pulse-echo ultrasound imaging systems which are used with probes which are inserted into or through body tissue and maneuvered so that a selected portion of that probe is within the imaged area. Aspiration biopsy is one example of such a procedure.

In aspiration biopsy, a small, hollow needle is inserted directly into the body to a desired point, whereupon a tissue sample is withdrawn, such as by vacuum aspiration. The needle is then withdrawn, but because of its relatively insignificant diameter, wound closure occurs normally by muscular and tissue tension, generally without the need for sutures, cauterization, or the like. For optimal effectiveness, aspiration biopsy techniques require that the tip of the needle be precisely accurately placed at the location of the tissues to be sampled. When properly performed, these techniques are safe, effective, and minimally traumatic.

Other common diagnostic and therapeutic procedures involving the manuevering of a probe through body tissues include various catheterization procedures. In these procedures, a catheter is maneuvered through a vein, artery, or other duct to a desired internal location. Such procedures include arterial angioplasty, thrombus removal, bile duct clearage, etc.

Various radiological (i.e. X-ray fluoroscopic) techniques have been utilized for ascertaining or estimating the location of tissue to be treated, sampled or diagnosed, and for aiding in the maneuvering of a given probe to its desired body location. These radiological techniques not only suffer from dimensional/accuracy limitations, but also from other inherent drawbacks related to the radiation doses involved in performing such procedures.

More recently, a variety of ultrasound imaging techniques have been suggested, particularly for in vivo imaging of relatively deep soft body tissue. Such ultrasound techniques include conventional A-mode, B-mode, and C-mode approaches. Because of their superior imaging capability with minimal hazard or risk to the patient, such techniques have achieved prominent use, particularly for needle location during aspiration biopsy techniques.

In one class of prior art aspiration biopsy systems, exemplified by U.S. Pat. Nos. 3,721,227 (Larson et al.), 4,108,165 (Copp et al.), 4,029,084 (Soldner), and German Pat. No. 42 55 401 (Vindenskaber), a biopsy needle is inserted in the center of an ultrasound transducer or transducer array, parallel to the direction of propagation of the ultrasound energy, so that the biopsy needle shows on the ultrasound image only if it diverts from such parallel orientation.

In another class of prior art systems, exemplified by U.S. Pat. No. 4,058,114 (Soldner), the biopsy needle is carried by angular aiming apparatus which in turn is mechanically coupled to a pointer overlying the ultrasound image field. As the needle angle is established, the pointer overlays the image and follows the progress of the needle.

In yet another class of prior art systems, exemplified by U.S. Pat. Nos. 3,556,079 (Omizo) and 4,429,539 (Vilkomerson at al.), a transducer element at the skin and another one within or at the tip of the needle correspond with one another to precisely locate the needle in the image field. In such systems, the needle is normally insertable into the body at an angle and in a direction which is completely independent from the angle and the position of the pulse-echo ultrasound imaging system. Accordingly, while such systems are effective at imaging the needle once the tip is disposed within the ultrasonically illuminated scan plane (imaging field), difficulties may be encountered in locating the needle in the scan plane for illumination and imaging.

These prior art systems have experienced a certain degree of commercial success, and are normally effective for their intended uses. Perhaps the least efficient of these systems are those which require parallel orientation of the propagating ultrasound energy and the needle, because of their failure to yield either clear composite images or accurate needle depth representation. While the systems of U.S. Pat. No. 4,429,539 (Vilkomerson et al.) are among the most effective, such systems do generally require special electronics and compact, expensive transducer elements which are mountable at the needle tip and removable through the biopsy needle.

SUMMARY OF THE INVENTION

The present invention represents an improvement in the Vilkomerson et al. type imaging systems. This improvement aids in positioning a probe within the scan plane by providing directional information to the user concerning the relative scan-plane and probe locations. The present invention thus provides a novel system for ensuring that the tip of a probe, such as a biopsy needle or catheter, may be readily positioned within the scan plane of an external pulse-echo imaging system during the insertion of the probe into or through body tissue which is to be subjected to a therapeutic or diagnostic procedure.

In accordance with the preferred embodiment of the present invention, a plurality of detector-transducers are spacially oriented at distinct probe locations, and are discretely connected to circuit means for sensing the sequence of arrivals of ultrasound waves at such locations. Such sequences are indicative of the probe position with respect to the scan plane, and are use to indicate the direction in which the scan plane or probe should be moved in order to cause the probe to fall within the scan plane.

Accordingly, a primary object of the present invention is the provision of an improved ultrasound imaging system for use with internal tissue probes, such as aspiration biopsy needles.

A further object of this invention is the provision of such a system wherein directional information concerning probe-scan plane locations is provided to the user.

These and other objects of the present invention will become apparent from the following, more detailed description.

BRIEF DESCRIPTION OF THE DRAWINGS

FIG. 3 is a block diagram of the preferred embodiment sequence and direction indicator logic illustrated in FIG. 1.

BEST MODE FOR CARRYING OUT THE INVENTION

Figure 1:
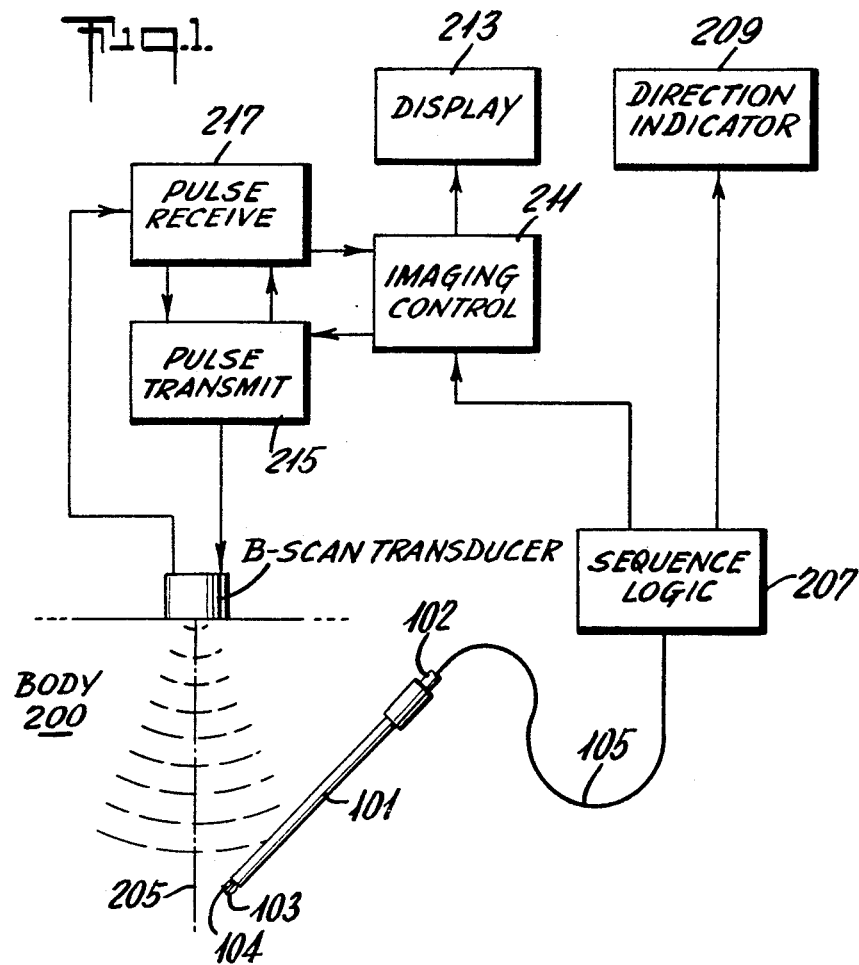
FIG. 1 is a block diagram of the preferred embodiment of the present invention showing the tip of an aspiration needle fitted with two detector-transducers disposed slightly to the right of a scan plane produced by a conventional B-scan pulse-echo imaging system.

Referring to FIG. 1, an aspiration needle system useful in accordance with the principles of the present invention is illustrated. In this embodiment, the probe comprises a conventional aspiration needle 101 which is hollow in the center and useful for vacuum aspiration of tissue samples once the needle is in place. In other embodiments, the aspiration needle may be replaced with a catheter when the probe is to be inserted through an existing body opening such as an artery, duct or canal. In the embodiment of FIG. 1, the hollow axial channel formed by needle 101 is useful in accordance with the present invention to receive an elongated support which carries a plurality of small, essentially point source, omni-directional transducers 103 and 104 which are disposed on opposite sides of the tip of an elongated support 102. Elongated support 102 also contains appropriate leads (not shown) from the transducers 103 and 104 to external transponder apparatus. Accordingly, the needle assembly of this imbodiment may be inserted directly into human tissue as the needle 101 conventionally would be done, whereby the transducers 103 and 104 will, in accordance with the principles of the present invention, be utilized to indicate the location of the tip of the needle with respect to the scan plane produced by an external pluse-echo ultrasound imaging system.

Figure 2:
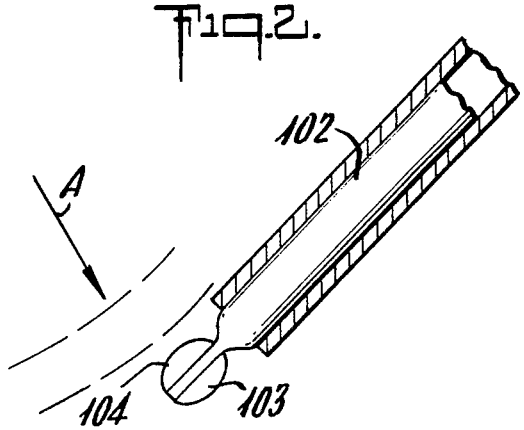
FIG. 2 is a greatly enlarged cross-section of the tip of the aspiration needle illustrated in FIG. 1.

Small, omni directional transducers which function essentially as point sources/receivers are commercially available, and typically are hemispherical in shape, as shown in FIG. 2. It will be appreciated that the actual size of the transducer 103 and its support 102 will be determined by the dimensions of the needle or catheter with which such transducers are used. It is anticipated that upon appropriate positioning of the needle or other probe within the body tissue being scanned, the entire mechanism 102, 103 and 104 may be withdrawn from the needle or other probe to thereby permit the interior of the probe to be used in another manner, as for example to aspirate or inject materials therethrough. Hence, the support 102 for the transducers 103 and 104 functions not only as a physical and electrical connection to external apparatus, but also as means for withdrawing the transducers from the probe.

Since the directional indications produced through the system of the present invention are dependent upon the directional orientation of detection-transducers 103 and 104, it is preferred to provide indicia (not shown) at the remote end of support 102 which will enable the user to maintain the desired orientation of support 102, and therefore, the proper orientation of detector-transducers 103 and 104 with respect to scan plane 205. It is within the scope of the present invention, however, to collect additional directional information from the detector-transducers by changing the relative positions of these transducers with respect to the scan plane, as for example by rotating support 102 about its axis. By determining the orientations at which a given one of the detector-transducers no longer is first insonified, it may be estimated that the scan plane is located in the direction of an axis which bisects these points. Alternatively, it is within the scope the present invention to provide more than 2 detector-transducers to provide additional directional information. Particularly when the probe is a catheter, such detector-transducers may be located along the body of the probe to provide additionally information concerning the position and orientation of portions of the probe within the body.

In FIG. 1, the preferred embodiment B-mode imaging system is illustrated which comprises a B-scan transducer 202 which is coupled to the body 200, and which ultrasonically illuminates an imaging field (perpendicular to the plane of the paper) along the scan axis 205. It will be understood that numerous such ultrasound imaging systems are commercially available, and the principles of the present invention are not limited to any particular one, or to any particular operational mode of transducer 202, whether transducer motion, transducer signal phasing, combination of these, or the like should be employed. Likewise, it is understood that signals to and from the transducer 202 may be coupled with the body 200 in any of a variety of well-known ways, including water paths, gel-type coupling media, and the like. As shown in FIG. 1, needle 101 has penetrated the body 200 and the point thereof, including transducers 203 and 204 are located in the vicinity of, but not within the scan plane 205. Nonetheless, transducers 103 and 104 will receive some ultrasonic waves from transducer 202 which will result in electrical signals being transferred along connecting cables 105 to sequence logic 207.

Sequence logic 207 distinguishes which of detector-transducers 103 and 104 is first insonified. This determination permits the user to ascertain the relative location of the scan plane 205 with respect to the detector-transducers 103 and 104, thereby permitting an adjustment in the scan plane location, and/or in the location of transducers 103 and 104. In order to readily facilitate such relative repositioning of these components, a direction indicator 109 is provided which responds to the output of the sequence logic to inform the operator of the sensed position of the detector transducers with respect to the scan plane. In the preferred embodiment, the direction indicators may be audible tones, lights, or other indicia which permit the user to reposition the components of the system in response thereto.

In FIG. 3 a preferred sequence and detection indicator logic is illustrated wherein inputs from the left and right transducers are subjected to conventional signal conditioning circuits 301 and 303. Such signal conditioning routinely comprises amplification of the detector-transducers signals together with noise rejection conditioning, such as the noise rejection circuitry disclosed in connection with the point-source transducers of aforementioned U.S. Pat. No. 4,249,539. The output of these signal conditioning circuits then passes to a phase comparator 305 which selectively activates move-left or move-right indicators 307 or 309 in response to the sensed first arrival of signals at the left or right transducer. A bistable flip-flop 33 ensures that the appropriate indicator remains activated until a changed arrival sequence is detected. The preferred phase comparator is a comparator capable of determining the "lead" or "lag" phase relationship, and the time difference between the leading edges of the wave forms. Using such a comparator, the U output is high when the wave form detected from the left transducer leads the wave detected from the right transducer. When the wave form detected at the right tranducer leads the wave form detected from the left transducer, the D output is high, resulting in the activation of move right indicator 309. Such a comparator can detect a 3 nanosecond timing difference (delta t), which is equivalent, at an operating frequency of 3 MHz, to about 0.01 wave length. For transducers separated by 0.005 inches, it has been estimated that this degree of sensitivity will permit detection of an offset of about 2.4 mm when the needle is 6 cm deep in the body.

In view of the foregoing description, those of ordinary skill in the art will recognize that the particular signal conditioning circuits 301 and 303 selected for use in the sequence logic should preferably condition the wave form of the received signal to provide a reliable wave front to comparator 313. In such instances, for examples, signal conditioning may comprise differentiating the signals received from the transducers to produce spiked wave forms for transmission to comparator 313. In FIG. 3, representative square wave signals offset by a time (delta t) are illustrated for the phase comparator input, which, as illustrated, result in a "high" D output. The signal conditioned outputs from the left and right transducers is also provided through "or" gate 311 to the imaging control 211 illustrated in FIG. 1. In this respect, once the detector-transducers are disposed within the scan plane 205, these transducers may be utilized as if they were a single, omni-directional point-source transducer such as disclosed in U.S. Pat. No. 4,249,539. As such, the location of the tip of needle 101 may be displayed at display 213, which also displays the image which has been derived from the imaging control 211 in combination with pulse transmitter 215, pulse receiver 217, and the aforementioned B-scan transducer 202.

In accordance with an alternate embodiment of the present invention the sequence logic 207 will time the delay between the receipt of wave arrivals of the detector-transducers. Since different time delays will be experienced with different probe-scan orientations, such time delays may be correlated to the relative angle between the detector-transducers and the scan area. As the number and distance between detector-transducers increase, the desirability of timing delays between different detector-transducers to obtain further information concerning the direction of the scan plane increases.

As seen from the above, the present invention provides a novel approach to aiding a physician in guiding a tissue probe with respect to an ultrasound scan area by providing directional information which readily enables the tissue probe to be positioned within the scan area.

It will be evident to those of ordinary skill in the art that similar principles and identical signal processing and logic systems and circuits can be utilized in other systems in accordance with this invention wherein the detector-transducers located on the probe need not be removable from the probe through a channel therein (although such would not necessarily be a deleterious design factor).

It will further be appreciated that the foregoing presents preferred and illustrative embodiments of the principles of the present invention, but that numerous alternate embodiments will occur to those of ordinary skill in the art without departure from the spirit or scope of the present invention.

I claim:

1. Apparatus for performing medical procedures upon select, internal body tissues, comprising:
   (a) a pulse-echo ultrasound imaging system for imaging a scan area of the body including said tissues, said imaging means including first imaging transducer for acoustic coupling to the exterior of the body;
   (b) probe means for insertion into the body in the vicinity of said area in a direction which is independent of the angle and position of said first transducer means;
   (c) a plurality of second detector-transducers disposed at selected locations on said probe means for receiving pulses from said first transducer;
   (d) circuit means electrically coupled to said detector-transducers for sensing the sequence of arrival of ultrasonic waves at said locations;

whereby the relative directional position of said probe means with respect to said scan area may be determined.

2. The apparatus of claim 1 further comprising indicator means for indication of said relative directional position to said user.

3. The apparatus of claim 2 wherein said indicator means is a tone generator means for generating an audible tone.

4. The apparatus of claim 2 wherein said circuit means comprises a phase comparator means for determining the sequence of arrival of said waves.

5. The apparatus of claim 4 wherein said circuit means further comprises bistable means driven by said comparator means for selectively maintaining the relative directional indication of said indicator means until a different arrival sequence is detected by said phase comparator.

6. The apparatus of claim 5 wherein said circuit means further comprises signal conditioning means for increasing the signal to noise ratio of the signal received from said detector-transducers.

7. The apparatus of claim 6 wherein an output of said circuit means is electrically coupled to said imaging system to facilitate imaging of said probe.

8. The apparatus of claim 1 wherein said second transducer means is removably disposed in said probe means.

9. The apparatus of claim 1 wherein said probe means is an aspiration needle.

10. The apparatus of claim 1 wherein said probe means is a catheter.

* * * * *